United States Patent
Puig

(10) Patent No.: US 10,956,312 B2
(45) Date of Patent: Mar. 23, 2021

(54) LABORATORY SYSTEM

(71) Applicant: Roche Diagnostics Operations, Inc., Indianapolis, IN (US)

(72) Inventor: Albert Puig, Barcelona (ES)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 252 days.

(21) Appl. No.: 16/014,276

(22) Filed: Jun. 21, 2018

(65) Prior Publication Data
US 2018/0373622 A1    Dec. 27, 2018

(30) Foreign Application Priority Data

Jun. 27, 2017   (EP) ................................. 17382400

(51) Int. Cl.
| | | |
|---|---|---|
| G01N 35/00 | (2006.01) | |
| G16B 99/00 | (2019.01) | |
| G16H 10/40 | (2018.01) | |
| G06F 11/36 | (2006.01) | |
| H04L 29/08 | (2006.01) | |

(52) U.S. Cl.
CPC ......... G06F 11/3688 (2013.01); G01N 35/00 (2013.01); G01N 35/00871 (2013.01); G16B 99/00 (2019.02); G16H 10/40 (2018.01); H04L 67/12 (2013.01)

(58) Field of Classification Search
CPC ..... G06F 11/3688; G16H 10/40; G16B 99/00; G01N 35/00; G01N 35/00871; H04L 67/12
See application file for complete search history.

(56) References Cited

U.S. PATENT DOCUMENTS

| | | | |
|---|---|---|---|
| 6,055,487 A | 4/2000 | Margery et al. | |
| 7,996,172 B2* | 8/2011 | Bauer | G06F 19/366 |
| | | | 702/85 |
| 2008/0270187 A1 | 10/2008 | Fors et al. | |
| 2009/0130765 A1 | 5/2009 | Bauer et al. | |
| 2012/0109531 A1* | 5/2012 | Knafel | G01N 35/00871 |
| | | | 702/19 |

(Continued)

FOREIGN PATENT DOCUMENTS

WO    WO 2012/037079 A1 *   3/2012

Primary Examiner — Gregory J Toatley, Jr.
Assistant Examiner — Lynda Dinh
(74) Attorney, Agent, or Firm — Roche Diagnostics Operations, Inc.

(57) ABSTRACT

A laboratory system is disclosed. The laboratory system comprises a plurality of laboratories comprising one or more analytical instruments for performing a plurality of analytical tests ($T1$-$n$) and providing analytical test results ($TR1$-$n$) and a remote computer communicatively connected to the laboratories. Each of the laboratories is configured to define test result validation criteria ($C1$-$n$) for validating at least one of the analytical test results ($TR1$-$n$) associated with the respective analytical tests ($T1$-$n$) of one of the plurality of laboratories. The remote computer is configured to define a plurality of profiles ($P1$-$n$) of validation criteria, to assign the profiles ($P1$-$n$) of test result validation criteria ($C1$-$n$) to one or more of the laboratories (102), and to perform an automatic validation of groups ($G1$-$n$) of the analytical test results ($TR1$-$n$) according to the profiles ($P1$-$n$) of test result validation criteria ($C1$-$n$).

6 Claims, 6 Drawing Sheets

(56) References Cited

U.S. PATENT DOCUMENTS

| | | | |
|---|---|---|---|
| 2012/0166094 A1* | 6/2012 | Parkhurst | G01N 35/00613 |
| | | | 702/22 |
| 2013/0145299 A1 | 6/2013 | Steimle et al. | |
| 2014/0180601 A1* | 6/2014 | Frank | G16H 10/40 |
| | | | 702/19 |
| 2017/0177724 A1 | 6/2017 | Booker et al. | |

* cited by examiner

| P1-n | G1-n | C1-n | F1-n | L1-n |
|---|---|---|---|---|
| P1 | G1, ( T1, T2, T3 ) | C1 | TR1, TR2, TR3 | L1 |
|  | G2, ( T4, T5, T6 ) | C2 | TR4, TR5, TR6 |  |
| P2 | G3, ( T1, T5 ) | C3 | TR1, TR5 | L2 |
|  | G4, ( T2, T4 ) | C4 | TR2, TR4 |  |

| WA1-n | G1-n | C1-n | F1-n | L1-n |
|---|---|---|---|---|
| WA1 | G1, ( T1, T2, T3 ) | C1 | TR1, TR2, TR3 | L1 |
| WA2 | G1, ( T1, T2, T3 ) | C2 | TR1, TR2, TR3 | L2 |

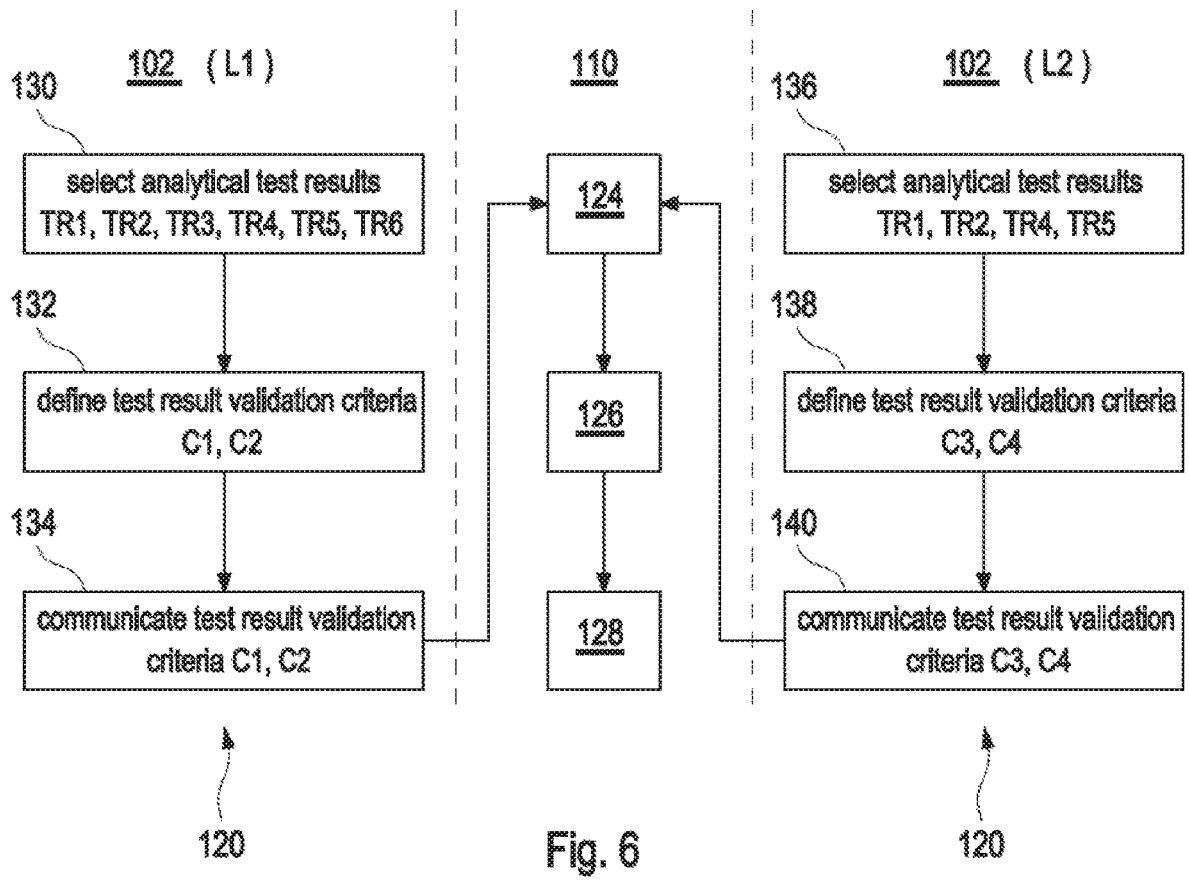
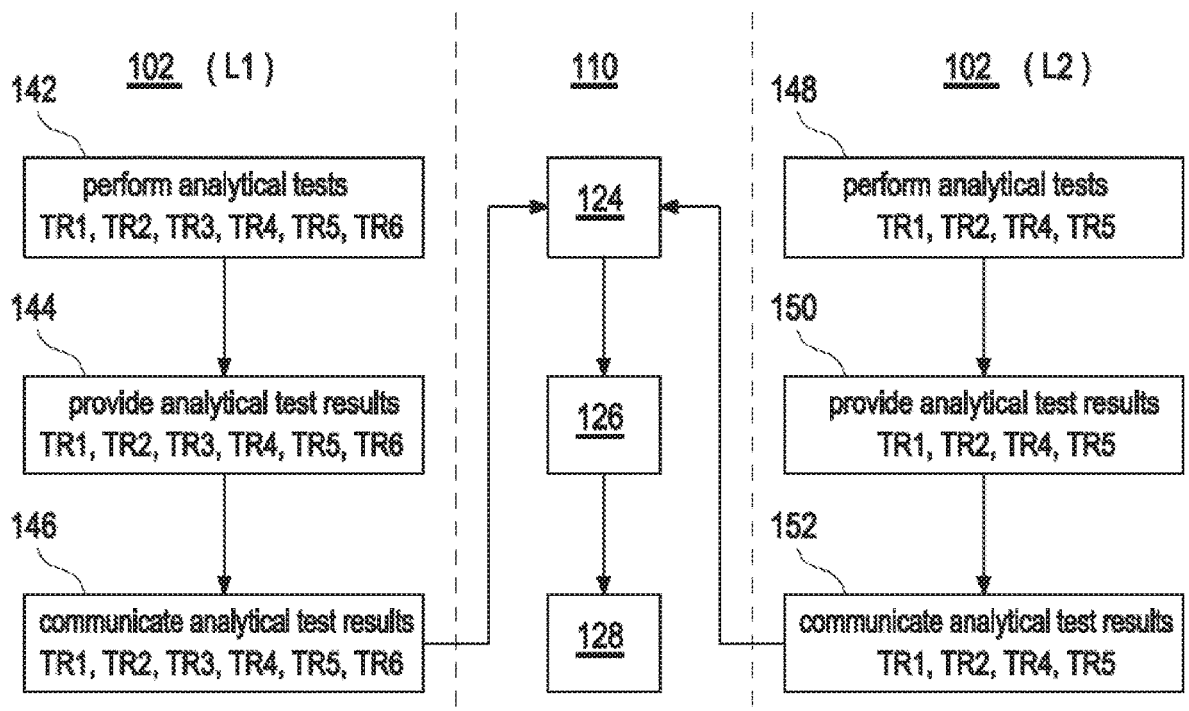

LABORATORY SYSTEM

CROSS-REFERENCE TO RELATED APPLICATIONS

This application is a continuation of EP 17382400.4 filed Jun. 27, 2017, which is hereby incorporated by reference.

BACKGROUND

The present disclosure generally relates to a laboratory system.

A Laboratory Information System (LIS) provides an essential support regarding managing test requests, receiving results and validating them in an efficient manner especially in the typical situation where a user might have distributed laboratories across several locations, this is the case when working in a multi-site environment.

One of the challenges faced by an LIS in a multi-site environment is the difficulties that are presented to a user when he needs to perform validation of different groups of test results with different validation criteria. In multi-site environments, the difficulty increases as there is need to create multiple configurations depending on the number of locations covered by the system. Thus, at each location, tests grouping is different and the validation criterion applied to each of those groups is also different.

Another of the challenges connected to a multi-site logic within a LIS is also to keep the performance of the system independent of the multiple configurations that are intrinsic to a multisite environment.

Therefore, there is a need to create profile logic within a validation workflow.

SUMMARY

According to the present disclosure, a laboratory system is presented. The laboratory system can comprise a plurality of laboratories. Each laboratory can comprise one or more analytical instruments for performing a plurality of analytical tests (T1-$n$) of biological samples and providing analytical test results (TR1-$n$). Each of the laboratories can be configured to define test result validation criteria (C1-$n$) for validating at least one of the analytical test results (TR1-$n$) associated with the respective analytical tests (T1-$n$) of one of the plurality of laboratories. The laboratory system can also comprise a remote computer communicatively connected to the laboratories via a communication network. The remote computer can be configured to define a plurality of profiles (P1-$n$) of validation criteria. Each profile (P1-$n$) can comprise a plurality of test result validation criteria (C1-$n$), a predetermined grouping (G1-$n$) of the plurality of analytical tests (T1-$n$) and a validation group flag (F1-$n$) indicating a group (G1-$n$) of analytical test results (TR1-$n$) to be validated. The remote computer can be configured to assign the profiles (P1-$n$) of test result validation criteria (C1-$n$) to one or more of the plurality of laboratories (102). The remote computer can be configured to perform an automatic validation of groups (G1-$n$) of the analytical test results (TR1-$n$) according to the profiles (P1-$n$) of test result validation criteria (C1-$n$) by setting the validation group flag (F1-$n$) to the groups (G1-$n$) of analytical test results (TR1-$n$) to be validated and validating the groups (G1-$n$) of analytical test results (TR1-$n$) onto which the validation group flag (F1-$n$) is set based on the test result validation criteria (C1-$n$).

Accordingly, it is a feature of the embodiments of the present disclosure to create profile logic within a validation workflow. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 6-10 illustrate respectively diagrams of sub-steps of the method of FIG. 5 according to an embodiment of the present disclosure.

DETAILED DESCRIPTION

Figure 1:
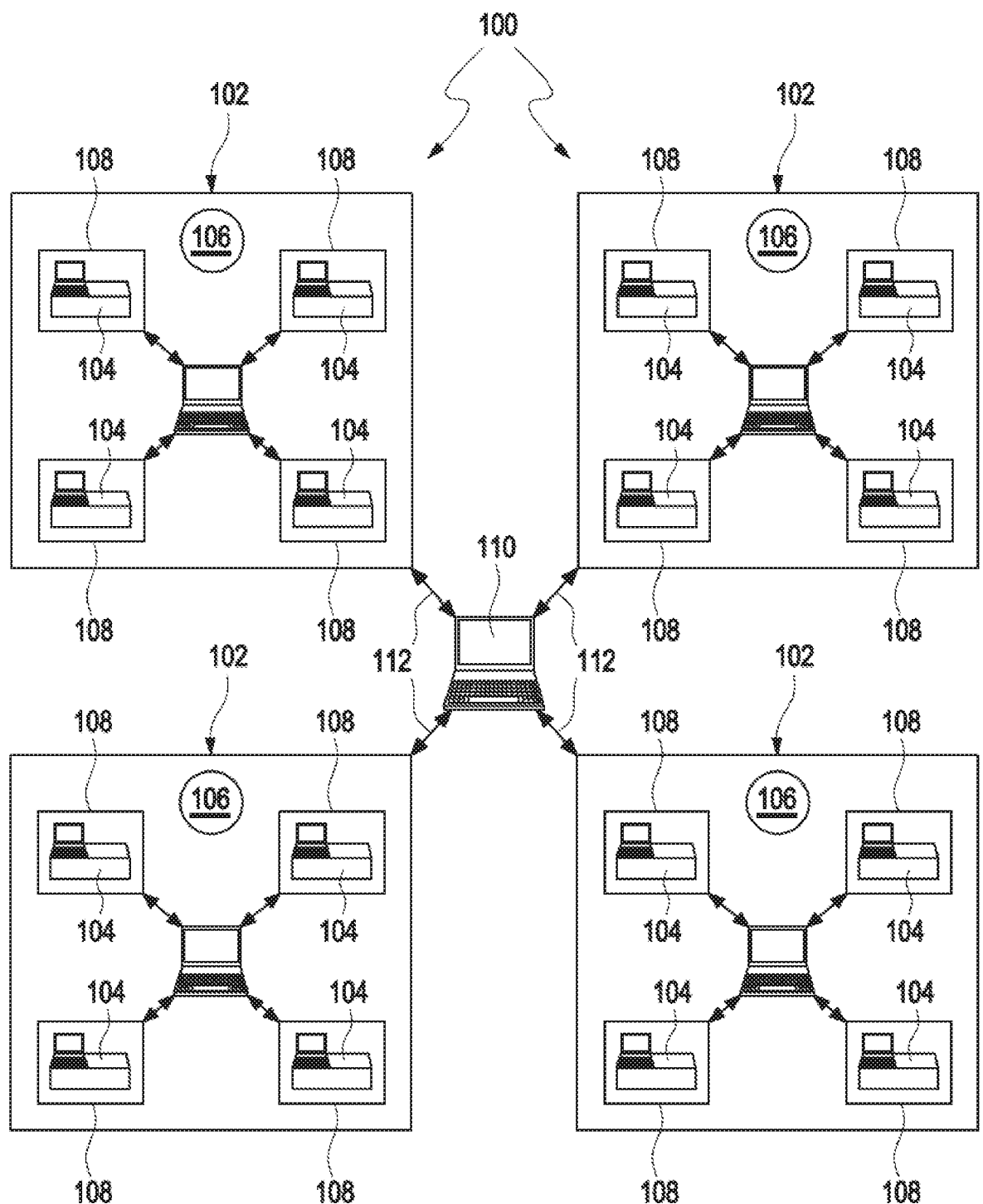
FIG. 1 illustrates a laboratory system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory system can comprise a plurality of laboratories. Each laboratory can comprise one or more analytical instruments for performing a plurality of analytical tests of biological samples and providing analytical test results. The laboratory system can also comprise a remote computer communicatively connected to the laboratories via a communication network. Each of the laboratories can be configured to define test result validation criteria for validating at least one of the analytical test results associated with the respective analytical tests of one of the plurality of laboratories. The remote computer can be configured to define a plurality of profiles of validation criteria. Each profile can comprise a plurality of the test result validation criteria, a predetermined grouping of the plurality of analytical tests and a validation group flag indicating a group of analytical test results to be validated. The remote computer can be configured to assign the profiles of validation criteria to one or more of the plurality of laboratories. The remote computer can be configured to perform an automatic validation of groups of the analytical test results according to the profiles of validation criteria by setting the validation group flag to the groups of analytical test results to be validated and validating the groups of analytical test results onto which the validation group flag can be set based on the test result validation criteria.

In multi-site environments for laboratories, each of the laboratories can be allowed to "design" or define its own validation criteria of laboratory test results. For example, for one or more analytical test results, a laboratory may define a validation criterion as appropriate. In other words, the validation criteria may be suitably adapted or adjusted by each laboratory. Thus, the validation criteria can be defined by the laboratories according to their expertise which can increase the quality of the validation results. However, with increasing size of such multi-site environments, a centralized control of results, validation and reporting can become very complex.

In order to address such challenges, some embodiments disclosed herein can make use of a remote computer configured to define a plurality of profiles of validation criteria. Each profile can comprise a plurality of the test result validation criteria, a predetermined grouping of the plurality of analytical tests and a validation group flag indicating a group of analytical test results to be validated. In other words, the remote computer can be used to take the validation criteria defined by the respective laboratories, to provide a certain grouping of the respective analytical tests and to provide a marker for those analytical tests results, which are to be validated, in order to create one or more profiles. These profiles can then be used for the validation of the groups of the analytical test results based on the test result validation criteria defined by the laboratories. Accordingly, contrary to a validation of each single analytical test result as known in the art, according to embodiments disclosed herein—a plurality of analytical test results can be validated as a group(s) based on test result validation criteria defined according to the requirements and expertise of the respective laboratories. Thus, the laboratory system can increase the throughput of validation processes per time and can also reduce the risks of user error, thereby providing consistency in the validation of test results across multiple laboratories.

The disclosed laboratory system can allow the creation of a "profile of validation criteria" which may comprise of a triad group of "validation criteria—test group—validate as a group". That is, an association between a given set of tests may be defined, a test result validation criteria specific and different from those used for other tests group and a flag setting if the group of tests has to be validated as one item, such as tests of the group will be validated only if all tests can be validated, or test by test. Then some of these associations "triads" of "test groups", "test result validation criteria" and "validate as a group flag" may be grouped under the "profile of validation criteria". Finally, the laboratory system can allow the assignment of these "profiles of validation criteria" to each of the existing locations in order to allow system to perform an automatic validation of a particular group of tests with different criteria depending on which location the tests have been done. The disclosed laboratory system can include both automatic validation performed by the system and manual validation by the user. The manual validation system can allow the user to select a group of tests of one or more locations and validate them with a specific test result validation criterion. In the end, the system—based on the location of the test—may apply an automatic validation of results based on remotely defined criteria. This automatic validation can trigger the sending of results for clinical validation or, in other cases, the emission of the report with the validated results.

The laboratory system may further comprise work areas defined for each of the laboratories. The work areas can be different from one another with respect to the analytical tests performable by the laboratories. The test result validation criteria can be allocated to the work areas.

Thus, the test result validation criteria may not only be assigned to a respective laboratory but may be assigned to a sub-level location or subdivision of a target operation. Thereby, the test result validation criteria may be designed to even smaller details or entities of a laboratory.

The work areas may be defined so as to comprise selective ones of the plurality of laboratories and/or subdivisions of the plurality of laboratories. Thus, each laboratory may be assigned to predetermined laboratories which in turn may be divided into several different locations. Thus, the work areas may be individually designed.

The test result validation criteria within a single work area may be identical. Thus, for a respective one of the work area, the same criteria can apply which can facilitate the validation.

The remote computer may be configured to allow a user to manually perform validation of groups of the analytical test results. Thus, a user may individually define the analytical test results to be validated.

The remote computer may be configured to allow a user to select groups of the analytical test results to be validated. Thus, the user may individually select the analytical test results to be validated.

The remote computer may be configured to adjust the test result validation criteria based on a validation criteria adjustment schedule. Thus, the test result validation criteria may be adjusted if desired. It can be noted that test result validation criteria may be clinical, technical or both.

The laboratories may be spatially separated from one another and wherein the plurality of profiles of validation criteria may be assigned to geographical locations of corresponding laboratories. Thus, with the disclosed laboratory system, even laboratories spaced apart from one another, even with large distances, can provide or accomplish the above described advantages.

According to the disclosed computer implemented method for validating a group of analytical test results of a plurality of analytical tests of biological samples performed by analytical instruments of a plurality of laboratories is presented. The method can comprise defining test result validation criteria for validating at least one of the analytical test results associated with the respective one of the laboratories, performing analytical tests of biological samples by at least one of the analytical instruments of the laboratories and defining profiles of test result validation criteria. Each profile can comprise one or more test result validation criteria, a predetermined grouping of the plurality of analytical tests and a validation group flag indicating a group of analytical test results to be validated. The method can also comprise assigning the profiles of validation criteria to one or more of the plurality of laboratories and performing an automatic validation of groups of the analytical test results by the remote computer according to the profiles of validation criteria by setting the validation group flag to the groups of analytical test results to be validated and validating the groups of tests onto which the validation group flag is set based on the test result validation criteria.

According to the disclosed computer-readable medium, the computer-readable medium can store instructions thereon which when executed by a computer system make the computer system perform the method described above.

According to the disclosed computer program product, the computer program product can have program code, in order to perform the method described above.

The disclosed system/method can further disclose and propose a computer program including computer-executable instructions for performing the method according to the disclosed system in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, particularly by using a computer program.

The disclosed system/method can further disclose and propose a computer program product having program code, in order to perform the method according to the disclosed system in one or more of the embodiments enclosed herein when the program is executed on a computer or computer network. Specifically, the program code may be stored on a computer-readable data carrier.

Further, the disclosed system/method can disclose and propose a data carrier having a data structure stored thereon, which, after loading into a computer or computer network, such as into a working memory or main memory of the computer or computer network, may execute the method according to one or more of the embodiments disclosed herein.

The disclosed system/method can further propose and disclose a computer program product with program code stored on a machine-readable carrier, in order to perform the method according to one or more of the embodiments disclosed herein, when the program is executed on a computer or computer network. As used herein, a computer program product can refer to the program as a tradable product. The product may generally exist in an arbitrary format, such as in a paper format, or on a computer-readable data carrier. Specifically, the computer program product may be distributed over a data network.

Finally, the disclosed system/method can propose and disclose a modulated data signal which can contain instructions readable by a computer system or computer network, for performing the method according to one or more of the embodiments disclosed herein.

Referring to the computer-implemented aspects of the disclosed system/method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the disclosed system can further disclose:

a computer or computer network comprising at least one processor, wherein the processor is adapted to perform the method according to one of the embodiments described, a computer loadable data structure adapted to perform the method according to one of the embodiments described while the data structure is executed on a computer, a computer program, wherein the computer program is adapted to perform the method according to one of the embodiments described while the program is executed on a computer, a computer program comprising a program for performing the method according to one of the embodiments described while the computer program is executed on a computer or on a computer network, a computer program comprising a program according to the preceding embodiment, wherein the program is stored on a storage medium readable to a computer, a storage medium, wherein a data structure is stored on the storage medium and wherein the data structure is adapted to perform the method according to one of the embodiments described after having been loaded into a main and/or working storage of a computer or of a computer network, and a computer program product having program code, wherein the program code can be stored or is stored on a storage medium, for performing the method according to one of the embodiments described, if the program code is executed on a computer or on a computer network.

A laboratory system can comprise a plurality of laboratories. Each laboratory can comprise one or more analytical instruments for performing a plurality of analytical tests of biological samples and provide analytical test results. The laboratory system can also comprise a remote computer communicatively connected to the laboratories via a communication network. Each of the laboratories can be configured to define test result validation criteria for validating at least one of the analytical test results associated with the respective analytical tests of one of the plurality of laboratories. The remote computer can be configured to define a plurality of profiles of validation criteria. Each profile can comprise a plurality of test result validation criteria, a predetermined grouping of the plurality of analytical tests and a validation group flag indicating a group of analytical test results to be validated. The remote computer can be configured to assign the profiles of validation criteria to one or more of the plurality of laboratories. The remote computer can be configured to perform an automatic validation of groups of the analytical test results according to the profiles of validation criteria by setting the validation group flag to the groups of analytical test results to be validated and validating the groups of analytical test results onto which the validation group flag is set based on the test result validation criteria.

The laboratory system can further comprise work areas defined for each of the laboratories. The work areas can be different from one another with respect to the analytical tests performable by the laboratories. The test result validation criteria can be allocated to the work areas.

The work areas can be defined so as to comprise selective ones of the plurality of laboratories and/or subdivisions of the plurality of laboratories.

The test result validation criteria within a single work area can be identical.

The remote computer can be configured to allow a user to manually perform validation of groups of the analytical test results.

The remote computer can be configured to allow a user to select groups of the analytical test results to be validated.

The remote computer can be configured to adjust the test result validation criteria based on a validation criteria adjustment schedule.

The laboratories can be spatially separated from one another. The plurality of profiles of validation criteria can be assigned to geographical locations of corresponding laboratories.

A computer implemented method for validating a group of analytical test results of a plurality of analytical tests of biological samples performed by analytical instruments of a plurality of laboratories can comprise defining test result validation criteria for validating at least one of the analytical test results associated with the respective one of the laboratories, performing analytical tests of biological samples by one of the analytical instruments of the laboratories, and defining profiles of test result validation criteria. Each profile can comprise one or more test result validation criteria, a predetermined grouping of the plurality of analytical tests and a validation group flag indicating a group of analytical test results to be validated. The method can also comprise assigning the profiles of validation criteria to one or more of the plurality of laboratories and performing an automatic validation of groups of the analytical test results by the remote computer according to the profiles of validation criteria by setting the validation group flag to the groups of analytical test results to be validated and validating the groups of tests onto which the validation group flag is set based on the test result validation criteria.

A computer-readable medium storing instructions thereon which when executed by a computer system make the computer system perform the steps of the above method.

A computer program product having program code to perform the above method.

As used in the following, the terms "have", "comprise" or "include" or any arbitrary grammatical variations thereof can be used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it can be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" may not be repeated, non-withstanding the fact that the respective feature or element may be present once or more than once.

Further, as used in the following, the terms "particularly", "more particularly", "specifically", "more specifically" or similar terms can be used in conjunction with additional/alternative features, without restricting alternative possibilities. Thus, features introduced by these terms can be additional/alternative features and are not intended to restrict the scope of the claims in any way. The present disclosure may, as the skilled person will recognize, be performed by using alternative features. Similarly, features introduced by "in an embodiment" or similar expressions can be intended to be additional/alternative features, without any restriction regarding alternative embodiments, without any restrictions regarding the scope and without any restriction regarding the possibility of combining the features introduced in such way with other additional/alternative or non-additional/alternative features.

The term "laboratory system" as used herein can refer to an assembly of at least two laboratories. The term "laboratory" in turn as used herein can refer to a facility that provides controlled conditions in which scientific or technological research, experiments, and measurements may be performed.

The term "analytical instrument" as used herein can refer to a device configured to obtain a measurement value and may also be called analyzer. An analytical instrument can be operable to determine via various chemical, biological, physical, optical or other technical procedures a parameter value of the sample or a component thereof. An analytical instrument may be operable to measure the parameter of the sample or of at least one analyte and return the obtained measurement value. The list of possible analysis results returned by the analytical instrument can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analytical instrument may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analytical instrument may comprise a process and detection system whose workflow can be optimized for certain types of analysis. Examples of such analytical instruments can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term "validation" as used herein can refer to a process of ensuring that an analytical test result is plausible. It can use routines, often called "validation criteria", "validation rules" "validation constraints" or "check routines", that check for correctness, meaningfulness, and security of data that are included in the analytical test result. The criteria may be automatically implemented through the remote computer, or by the inclusion of explicit application program validation logic operated by a user. Thus, validation can mean a check whether the test result satisfies the validation criterion assigned thereto and it can be said to be invalid or to have failed the validation if the test result does not satisfy the validation criterion.

The term "test result validation criteria" as used herein can refer to criteria used for validating at least one test result of an analytical test. The criteria may be a threshold of test result, a range of an acceptable test result or any other aspect allowing to evaluate the test result.

The term "work area" as used herein can refer to a location to which an operation or job to be carried out is assigned.

The term "subdivision" as used herein can refer to an entity of a laboratory. For example, a laboratory can be divided into predetermined subdivisions. The reason for the provision of subdivisions can exist for organizational reasons such as the assigning of the performance of different analytical tests to subdivisions or operational procedures in order to increase the efficiency of the laboratory output.

The term "sub-level location" as used herein can refer to a location of a lower level of a certain location. For example, a location may be divided into even smaller locations. For example, a laboratory may be present at a certain location such as a city or building, wherein the sub-level locations of this location can be different locations in this city or building.

FIG. 1 shows a laboratory system 100. The laboratory system 100 can comprise a plurality of laboratories 102. Each laboratory 102 can comprise one or more analytical instruments 104 for performing a plurality of analytical tests of biological samples and provide analytical test results. The laboratories 102 can be located at different locations 106. For example, the laboratory system 100 can comprise four locations 106, each of which can comprise one laboratory 102. It can be noted that the number of laboratories 102 may be less or more than four such as two, three, five, six or even more. The locations 106 can be spatially separated from one another. The laboratory system 100 can further comprise work areas 108 defined for each of the laboratories 102. The work areas 108 can be different from one another with respect to the analytical tests performable by the laboratories 102. For example, each laboratory 102 can comprise four work areas 108. It can be noted that the number of work areas 108 for each of the laboratories 102 may be less or more than four such as two, three, five, six or even more. The work areas 108 can be defined so as to comprise selective ones of the plurality of laboratories 102 and/or subdivisions of the plurality of laboratories 102. Each of the laboratories 102 can be configured to define test result validation criteria for validating at least one of the analytical test results associated with the respective analytical tests of one of the plurality of laboratories 102. For example, each laboratory 102 may include a computer having an input device such as a keyboard for inputting the definition of test result validation criteria. The test result validation criteria within a single work area 108 can be identical. The test result validation criteria may be allocated to the work areas 108.

The laboratory system 100 can further comprise a remote computer 110 communicatively connected to the laboratories 102 via a communication network 112. The communication network 112 may include a wired or wireless connection of the remote computer 110 and the laboratories 102. For example, the communication network 112 may include a connection by the world wide web. The remote computer 110 can be configured to define a plurality of profiles P1-$n$ of validation criteria as will be explained in further detail below. It is to be noted that n is an integer greater than 1.

Figures 2, 3, 4:
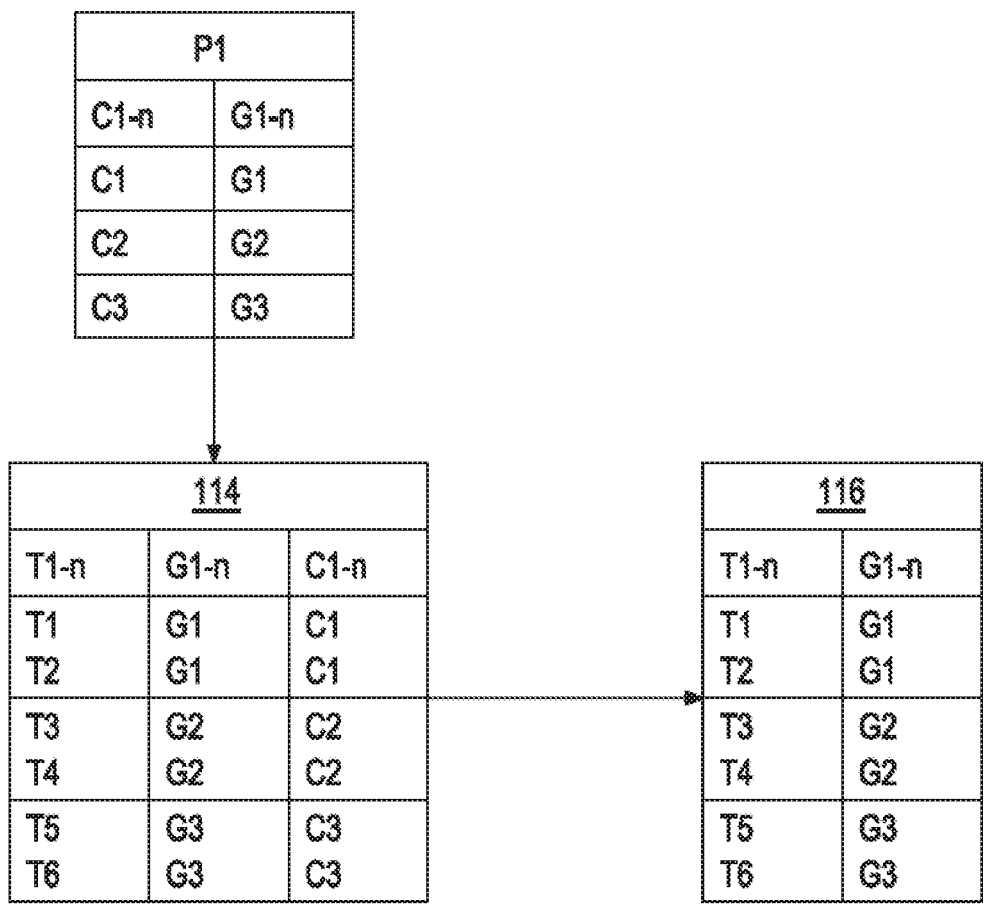
FIG. 2 illustrates an example for profiles of validation criteria according to an embodiment of the present disclosure.
FIG. 3 illustrates examples for the allocation of validation criteria to work areas according to an embodiment of the present disclosure.
FIG. 4 illustrates a block diagram of a method carried out by the laboratory system according to an embodiment of the present disclosure.

FIG. 2 shows an example for profiles P1-$n$ of validation criteria defined by the remote computer 110. Each profile P1-$n$ can comprise a plurality of the test result validation criteria C1-$n$, a predetermined grouping G1-$n$ of the plurality of analytical tests T1-$n$ and a validation group flag F1-$n$ indicating a group G1-$n$ of analytical test results TR1-$n$ to be validated. It can be noted that n is respectively an integer greater than 1. The plurality of profiles P1-$n$ of validation criteria can be assigned to geographical locations L1-$n$ of corresponding laboratories 102. The remote computer 110 can be configured to assign the profiles P1-$n$ of validation criteria to the one or more of the laboratories 102. The remote computer 110 can be configured to perform an automatic validation of groups G1-$n$ of the analytical test results according to the profiles P1-$n$ of validation criteria by setting the validation group flag F1-$n$ to the groups G1-$n$ of analytical tests to be validated and validating the groups of test results TR-1$n$ onto which the validation group flag F1-$n$ is set based on the test result validation criteria C1-$n$. Optionally, each laboratory 102 may be configured to send the test result validation criteria to the remote computer 110.

As mentioned above, the laboratories 102 can be configured to perform plurality of analytical tests by the respective analytical instruments 104. In the shown example, six analytical tests T1, T2, T3, T4, T5, T6 may be performed. The analytical tests T1-T6 may be grouped. For example, profile P1 can comprise a first group G1 and a second group G2. Group G1 can include analytical tests T1, T2, T3 and group G2 includes analytical tests T4, T5, T6. For group G1, test result validation criterion C1 can be defined. For group G2, test result validation criterion C2 can be defined. Profile P1 can be assigned to location L1. Further, profile P2 can comprise a third group G3 and a fourth group G4. Group G3 can include analytical tests T1 and T5 and group G4 can include analytical tests T2 and T4. For group G3, test result validation criterion C3 can be defined. For group G4, test result validation criterion C4 can be defined. Profile P2 can be assigned to location L2. With this configuration, the laboratory system 100 may operate so that the analytical test T1 at location L1 can be validated using test result validation criterion C1 whereas the analytical test T1 at location L2 can be validated using criteria C2.

The remote computer 110 can be configured to allow a user to manually perform validation of groups of the analytical test results TR1-$n$. Further, the remote computer 110 can be configured to allow a user to select groups G1-$n$ of the analytical test results TR1-$n$ to be validated. The remote computer 110 can be configured to adjust the test result validation criteria C1-$n$ based on a validation criteria adjustment schedule. The test result validation criteria C1-$n$ may be clinical, technical or both.

FIG. 3 shows examples for the allocation of test result validation criteria C1-$n$ to work areas WA1-$n$. It can be noted that n is an integer greater than 1. As mentioned above, the work areas WA1-$n$ can be different from one another with respect to the analytical tests performable by the laboratories 102. The work areas WA1-$n$ can be defined so as to comprise selective ones of the plurality of laboratories 102 and/or subdivisions of the plurality of laboratories. The test result validation criteria C1-$n$ within a single work area WA1-$n$ can be identical. FIG. 3 shows a first work area WA1 to which a group G1 of three analytical tests T1, T2, T3 is allocated. The analytical tests T1, T2, T3 may be performed at location L1 for which test result validation criterion C1 is defined. FIG. 3 also shows a second work area WA2 to which the group G1 of three analytical tests T1, T2, T3 is allocated. The analytical tests T1, T2, T3 may be performed at location L2 for which test result validation criterion C2 is defined. With this configuration, for example, the test result TR1 of test T1 in location L1 can be validated using the test result validation criterion C1, whereas the test result TR1 of test T1 in location L2 can be validated using the test result validation criterion C2.

FIG. 4 shows a block diagram of an operation carried out by the laboratory system 100. A profile P1 of test result validation criteria is defined in that the profile P1 can include test result validation criteria C1, C2, C3 assigned to groups G1, G2, G3. The laboratories 102 may perform analytical tests T1, T2, T3, T4, T5, T6, the results TR1, TR2, TR3, TR4, TR5, TR6 of which are all to be validated at the same time. Analytical tests T1 and T2 can be assigned to group G1. Analytical tests T3 and T4 can be assigned to group G2. Analytical tests T5 and T6 can be assigned to group C3. An order 114 for validating all results TR1-6 of the analytical tests T1, T2, T3, T4, T5, T6 may be validated with the profile P1. In other words, only one step may be necessary to validate the complete order 114 and reveal the validation result 116.

Figure 5:
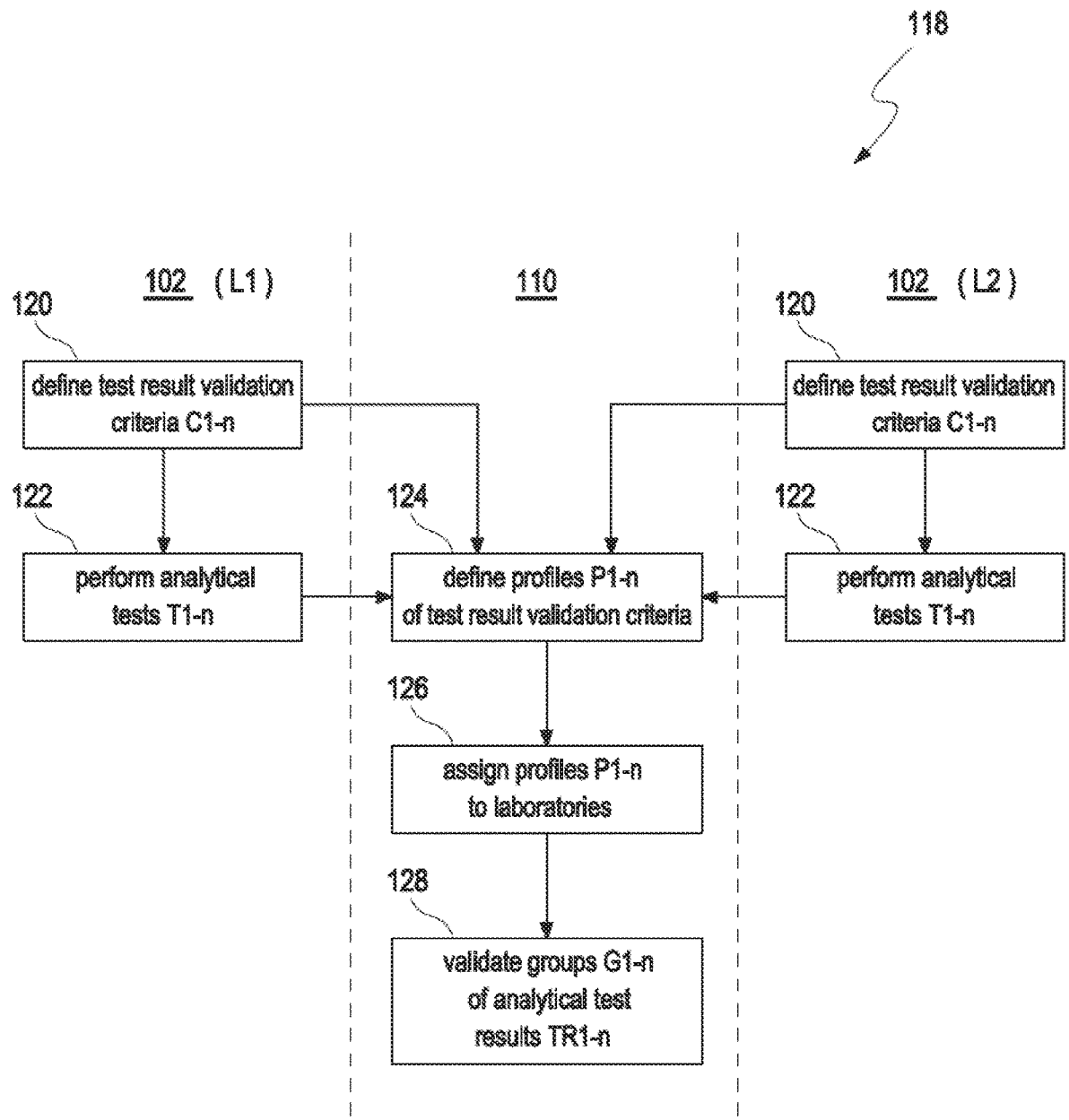
FIG. 5 illustrates a swim line diagram of a method for validating a group of analytical test results of a plurality of analytical tests of biological samples performed by analytical instruments of a plurality of laboratories according to an embodiment of the present disclosure.

FIG. 5 shows a swim line diagram a method 118 for validating a group G1-$n$ of analytical test results TR1-$n$ of a plurality of analytical tests T1-$n$ of biological samples performed by analytical instruments 104 of a plurality of laboratories 102. The method may be computer implemented. For example, the method 118 can be performed by the remote computer 110 described above.

The method 118 can comprise the following basic steps which will be explained in further detail with reference to FIGS. 6 to 10. It can be noted that the method will be explained as an example only assuming that two laboratories 102 are present with the laboratory system. Thus, it can be clear that more than two laboratories 102 may be present such as three, four, five or even more laboratories 102. One of the two laboratories 102 can be located at a first location L1 and the other one can be located at a second location L2 different from the first location L1. Step 120 can include defining test result validation criteria C1-$n$ for validating at least one of the analytical test results TR1-$n$ associated with the respective one of the laboratories 102. The validation criteria C1-$n$ may be defined by the laboratories 102. Step 122 can include performing analytical tests T1-$n$ of biological samples by one of the analytical instruments 104 of the laboratories 102. Step 124 can include defining profiles P1-$n$ of test result validation criteria. The profiles P1-$n$ may be defined by the remote computer 110. Each profile P1-$n$ can comprise one or more test result validation criteria C1-$n$, a predetermined grouping G1-$n$ of the plurality of analytical tests T1-$n$ and a validation group flag F1-$n$ indicating a group of analytical test results TR1-$n$ to be validated. Step 126 can include assigning the profiles P1-$n$ of test result validation criteria C1-$n$ to the one or more of the laboratories 102. Step 128 can include performing an automatic validation of groups G1-$n$ of the analytical test results TR1-$n$ according to the profiles P1-$n$ of test result validation criteria C1-$n$ by setting the validation group flag F1-$n$ to the groups G1-$n$ of analytical test results TR1-$n$ to be validated and validating the groups G1-$n$ of analytical tests T1-$n$ onto which the validation group flag F1-$n$ is set based on the test result validation criteria C1-$n$. The automatic validation may be performed by the remote computer 110.

FIG. 6 shows a swim line diagram of step 120 of the above method. As mentioned above, one of the two laboratories 102 can be located at first location L1 and the other laboratory 102 can be located at second location L2. The laboratory 102 at first location L1 can be configured to perform six analytical tests T1, T2, T3, T4, T5, T6 resulting in the analytical test results TR1, TR2, TR3, TR4, TR5, TR6. The laboratory 102 at second location L2 can be configured to perform four analytical tests T1, T2, T4, T5 resulting in the TR1, TR2, TR4, TR5. Step 120 can include sub-step 130 in which the laboratory 102 at location L1 can select the analytical test results TR1, TR2, TR3, TR4, TR5, TR6 for process of defining test result validation criteria C1-$n$. In sub-step 132, the laboratory 102 at location L1 can define two validation criteria C1, C2. In sub-step 134, the laboratory 102 at location L1 can communicate the defined validation criteria C1, C2 to the remote computer 110. For example, the laboratory 102 at location L1 can send data including information on the validation criteria C1, C2 to the remote computer 110 via the communication network 112. Step 120 can also include sub-step 136 in which the laboratory 102 at location L2 can select the analytical test results TR1, TR2, TR4, TR5 for process of defining test result validation criteria C1-$n$. In sub-step 138, the laboratory 102 at location L2 can define two validation criteria C3, C4. In sub-step 140, the laboratory 102 at location L2 can communicate the defined validation criteria C3, C4 to the remote computer 110. For example, the laboratory 102 at location L2 can send data including information on the validation criteria C3, C4 to the remote computer 110 via the communication network 112. It can be noted that steps 130 to 134 and steps 136 to 140 may be carried out in a subsequent or simultaneous manner.

FIG. 7 shows a swim line diagram of step 122 of the above method. As mentioned above, the laboratory 102 at first location L1 can be configured to perform six analytical tests T1, T2, T3, T4, T5, T6, which can result in the analytical test results TR1, TR2, TR3, TR4, TR5, TR6. The laboratory 102 at second location L2 can be configured to perform four analytical tests T1, T2, T4, T5, which can result in the TR1, TR2, TR4, TR5. Step 122 can include sub-step 142 in which the laboratory 102 at location L1 can perform the analytical tests T1, T2, T3, T4, T5, T6 by its analytical instruments 104. In sub-step 144, the analytical instruments 104 of laboratory 102 at location L1 can provide the respective analytical test results TR1, TR2, TR3, TR4, TR5, TR6. In sub-step 146, the laboratory 102 at location L1 can communicate the analytical test results TR1, TR2, TR3, TR4, TR5, TR6 to the remote computer 110. For example, the laboratory 102 at location L1 can send data including information on the analytical test results TR1, TR2, TR3, TR4, TR5, TR6 to the remote computer 110 via the communication network 112. Step 122 can also include sub-step 148 in which the laboratory 102 at location L2 can perform the analytical tests T1, T2, T4, T5 by its analytical instruments 104. In sub-step 150, the analytical instruments 104 of laboratory 102 at location L2 can provide the respective analytical test results TR1, TR2, TR4, TR5. In sub-step 152, the laboratory 102 at location L2 can communicate the analytical test results TR1, TR2, TR4, TR5 to the remote computer 110. For example, the laboratory 102 at location L2 can send data including information on the analytical test results TR1, TR2, TR4, TR5 to the remote computer 110 via the communication network 112. It can be noted that steps 142 to 146 and steps 148 to 152 may be carried out in a subsequent or simultaneous manner.

Figure 8:
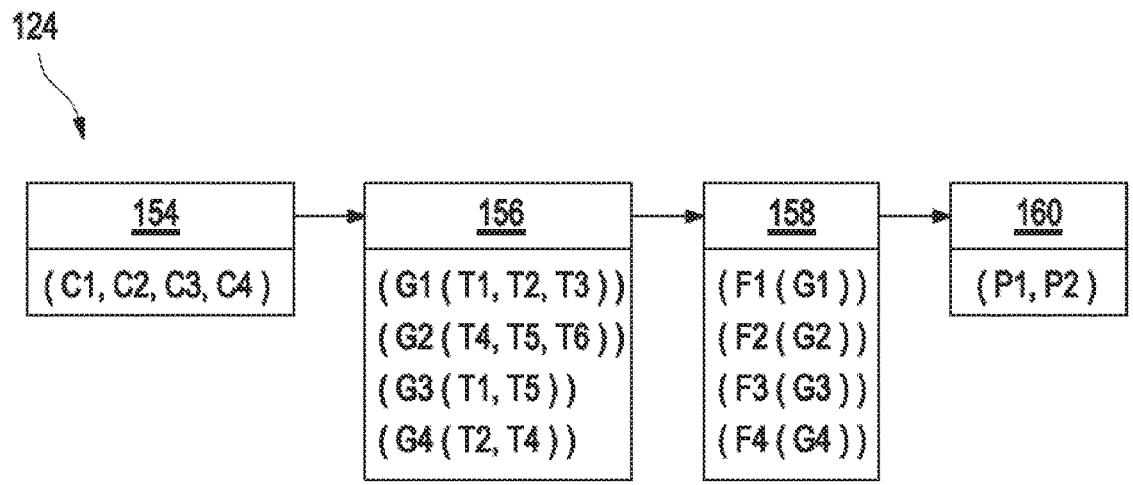

FIG. 8 shows a flow chart of step 124 of the above method. Step 124 can include sub-step 154, in which the remote computer 110 can select test result validation criteria C1-$n$ for the process of defining a profile P1-$n$ of the test result validation criteria C1-$n$. In the shown example, the remote computer 110 can select test result validation criteria C1, C2, C3, C4 provided by the laboratories 102 at locations L1, L2. In sub-step, 156, the remote computer 110 can create groups G1-$n$ of analytical tests T1-$n$. In the shown example, the remote computer 110 can create group G1 including analytical tests T1, T2, T3, group G2 including analytical tests T4, T5, T6, group G3 including analytical tests T1, T5 and group G4 including T2, T4. In sub-step 158, the remote computer 110 can create group flags F1-$n$ indicating a group G1-$n$ of analytical test results TR1-$n$ to be validated. In the shown example, the remote computer 110 can create group flag F1 including the analytical test results of group G1, group flag F2 including the analytical test results of group G2, group flag F3 including the analytical test results of group G3 and group flag F4 the analytical test results of group G4. Thereby, in sub-step 160, a profile P1 of test result validation criteria comprising test result validation criteria C1, C2, groups G1, G2 and group flags F1, F2, and a profile P2 of test result validation criteria comprising test result validation criterion C3, C4, groups G3, G4 and group flags F3, F4, can be defined.

Figure 9:
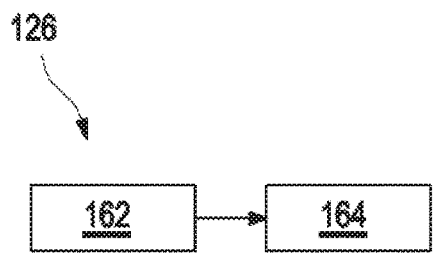

FIG. 9 shows a flow chart of step 126 of the above method. Step 126 can include sub-step 162, in which profile P1 of test result validation criteria can be assigned to the laboratory 102 at location L1, and sub step 164, in which profile P2 of test result validation criteria can be assigned to the laboratory 102 at location L2. It can be noted that steps 162 and 164 may be carried out in a subsequent or simultaneous manner.

Figure 10:
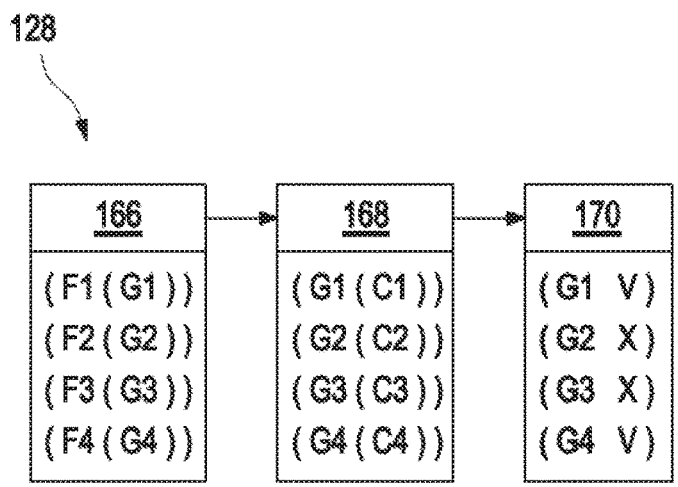

FIG. 10 shows a flow chart of step 128 of the above method. Step 128 can include sub-step 166, in which the validation group flag F1-$n$ is set to the groups G1-$n$ of analytical test results TR1-$n$ to be validated. In the shown example, group flag F1 can be set onto group G1, group flag F2 can be set onto group G2, group flag F3 can be set onto group G3 and group flag F4 can be set onto group G4. In sub-step 168, the groups G1-$n$ of analytical test results TR1-$n$ onto which the validation group flag F1-$n$ is set can be validated based on the test result validation criteria C1-$n$. In the shown example, group G1 can be validated based on test result validation criterion C1, group G2 can be validated based on based on test result validation criterion C2, group G3 can be validated based on based on test result validation criterion C3 and group G4 can be validated based on based on test result validation criterion C4. In sub-step 170, the result of the automatic validation of the groups G1-$n$ of analytical test results TR1-$n$ can be provided. With other words, each of the analytical test results TR1-$n$ can be checked whether it satisfies the validation test result validation criterion C1-$n$. It can be said to be invalid if the analytical test result does not satisfy the associated validation criterion C1-$n$. In the shown example, analytical test results TR1, TR2, TR3 of group G1 can be validated so as to satisfy test result validation criterion C1 as indicated by "V", analytical test results TR4, TR5, TR6 of group G2 can be validated so as not to satisfy test result validation criterion C2 as indicated by "X", analytical test results TR1, TR5 of group G3 can be validated so as not to satisfy test result validation criterion C3 as indicated by "X" and analytical test results TR2, TR4 of group G4 can be validated so as to satisfy test result validation criterion C4 as indicated by "V".

Figure 11:
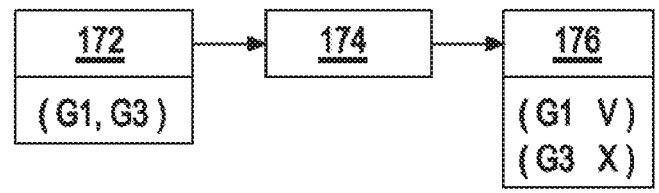
FIGS. 11-13 illustrate respectively further embodiments of the method of FIG. 5 according to an embodiment of the present disclosure.

FIG. 11 shows another embodiment of the method of FIG. 5. In addition to the automatic validation in step 128, by the remote computer 110, in step 172 a user may select groups G1-$n$ of the analytical test results TR1-$n$ to be validated. In the shown example, a user can select groups G1 and G3 in step 172. Thereby, the user may manually perform validation of groups G1-$n$ of the analytical test results TR1-$n$ by the remote computer 110 in step 174. In the shown example, manual validation of groups G1 and G3 can be performed. The remote computer can then provide the user with the validation result in step 176. In the shown example, group G1 can be indicated so as to be valid as indicated by "V" and group G3 is indicated so as not be valid as indicated by "X".

Figure 12:
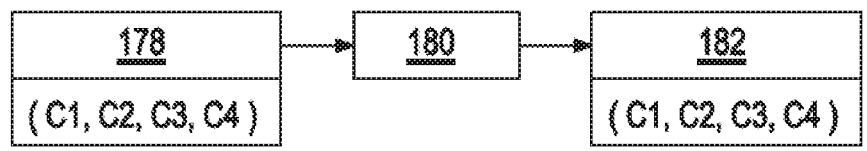

FIG. 12 shows another embodiment of the method of FIG. 5 which may be made alternatively or in addition to the one of FIG. 11. Before defining the profiles P1-$n$ in step 124, the remote computer 110 may adjust the test result validation criteria C1-$n$ based on a validation criteria adjustment scheudle. For example, in step 178, the remote computer 110 can receive the test result validation criteria C1, C2, C3, C4 from the laboratories 102. In step 180, the remote computer 110 can refer to a validation criteria adjustment schedule so as to adjust the test result validation criteria C1, C2, C3, C4. In step 182, the remote computer 110 can then provide adjusted test result validation criteria C'1-$n$. In the shown example, the remote computer can adjust test result validation criteria C1 and C3 so as to provide adjusted test validation test criteria C'1 and C'3. An adjustment of the test result validation criteria may be needed due to changes in the analytical tests, changes in the regulatory requirements, changes due to constant improvement of the validation criteria, quality control data or a reflex test result(s).

Figure 13:
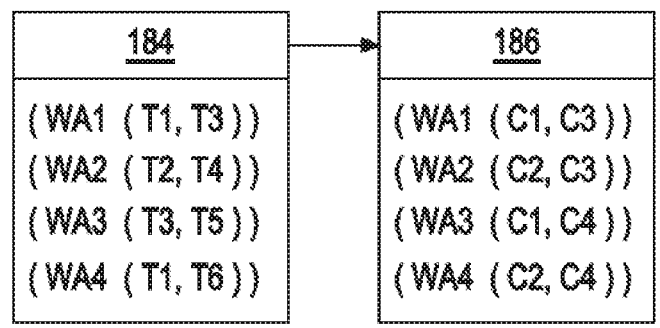

FIG. 13 shows another embodiment of the method of FIG. 5 which may be made alternatively or in addition to the ones of FIGS. 11 and 12. Before or after defining the test result validation criteria C1-$n$ in step 120, work areas WA1-$n$ can be defined for each of the laboratories 102. For example, in step 184 four work areas WA1, WA2, WA3, WA4 can be defined. The work areas WA1-$n$ may be defined by the laboratories 102. The work areas WA1, WA2, WA3, WA4 can be different from one another with respect to the analytical tests T1-$n$ performable by the laboratories 102. Particularly, the work areas WA1, WA2, WA3, WA4 can be defined so as to comprise selective ones of the plurality of laboratories 102 and/or subdivisions of the plurality of laboratories 102. For example, work area WA1 can comprise a laboratory 102 configured to perform analytical tests T1 and T3, work area WA2 can comprise a laboratory 102 configured to perform analytical tests T2 and T4, work area WA3 can comprise a laboratory 102 configured to perform analytical tests T3 and T5 and work area WA4 can comprise a laboratory 102 configured to perform analytical tests T1 and T6. The test result validation criteria C1-$n$ within a single work area WA1-$n$ can be identical. For example, test result validation criteria C1 and C3 in work area WA1 can be identical. In step 186, the test result validation criteria C1-$n$ can be allocated to the work areas WA1-$n$. For example, test result validation criteria C1 and C3 can be allocated to work area WA1, test result validation criteria C2 and C3 can be allocated to work area WA2, test result validation criteria C1 and C4 can be allocated to work area WA3 and test result validation criteria C2 and C4 can be allocated to work area WA4.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory system, the laboratory system comprising:
a plurality of laboratories, each laboratory comprising one or more analytical instruments performing a plurality of analytical tests of biological samples and providing analytical test results, wherein the one or more of analytical instruments of each laboratory is configured to define test result validation criteria for validating at least one of the analytical test results associated with respective to the analytical tests of one or more of the plurality of laboratories; and a remote computer communicatively connected to the laboratories via a communication network, wherein the remote computer is configured to:

define a plurality of profiles of validation criteria, each profile comprising a plurality of test result validation criteria, wherein the plurality of the test result validation criteria are allocated to work areas, wherein the work areas defined for the each of the laboratories and are different from one another with respect to the analytical tests performing by the one or more analytical instruments of the laboratories, a predetermined grouping of the plurality of analytical tests, and a validation group flag indicating a group of analytical test results to be validated;

assign the profiles of test result validation criteria to the one or more of the plurality of laboratories;

perform an automatic validation of groups of the analytical test results based on the profiles of the test result validation criteria by setting the validation group flag (F1-$n$) to the groups of the analytical test results to be validated and validating the groups of the analytical test results onto which the validation group flag is set based on the test result validation criteria;

the remote computer further configured to allow a user to manually perform the validation of the groups of the analytical test results by defining, selecting the analytical test results to be validated, and adjusting the test results validation criteria if desired; and thereby increasing quality of the analytical test results and providing consistency in the validation of test results across multiple laboratories.

2. The laboratory system according to claim 1, wherein the work areas are defined so as to comprise selective ones of the plurality of laboratories and/or subdivisions of the plurality of laboratories.

3. The laboratory system according to claim 1, wherein the test result validation criteria within a single work area are identical.

4. The laboratory system according to claim 1, wherein the laboratories are spatially separated from one another and wherein the plurality of profiles of validation criteria are assigned to geographical locations of corresponding laboratories.

5. A computer implemented method for validating a group of analytical test results of a plurality of analytical tests of biological samples performed by analytical instruments of a plurality of laboratories, the method performed by a remote computer connected to the laboratories via a communication network, comprising:

defining test result validation criteria for validating at least one of the analytical test results associated with respective one or more of the laboratories;

performing the analytical tests of the biological samples by one or more of the analytical instruments of the laboratories;

defining profiles of the test result validation criteria, each profile comprising one or more test result validation criteria, wherein the one or more test result validation criteria are allocated to work areas, wherein the work areas defined for the each of the laboratories and are different from one another with respect to the analytical tests performing by the one or more of the analytical instruments of the laboratories, a predetermined grouping of the plurality of analytical tests and a validation group flag (F1-$n$) indicating a group of the analytical test results to be validated;

assigning the profiles of the test result validation criteria to the one or more of the laboratories;

performing an automatic validation of groups of the analytical test results based on the profiles of the validation criteria by setting the validation group flag (F1-$n$) to the groups of the analytical test results to be validated and validating the groups of the analytical test results onto which the validation group flag is set based on the test result validation criteria;

the remote computer further configured to allow a user to manually perform the validation of the groups of the analytical test results by defining, selecting the analytical test results to be validated and adjusting the test results validation criteria as desired; and thereby increasing quality of the analytical test results and providing consistency in the validation of test results across multiple laboratories.

6. A non-transitory computer-readable medium storing instructions thereon which when executed by a computer system make the computer system perform the method according to claim 5.

* * * * *